US00RE38958E

(19) United States
(12) Reissued Patent
Stimac et al.

(10) Patent Number: US RE38,958 E
(45) **Date of Reissued Patent: *Jan. 31, 2006**

(54) METHODS AND FORMULATIONS FOR CONTROL OF PESTS

(75) Inventors: Jerry L. Stimac, Gainesville, FL (US); Roberto Pereira, Gainesville, FL (US)

(73) Assignee: University of Florida Research Foundation, Inc., Gainesville, FL (US)

( * ) Notice: This patent is subject to a terminal disclaimer.

(21) Appl. No.: 10/612,680

(22) Filed: Jul. 1, 2003

Related U.S. Patent Documents

Reissue of:
(64) Patent No.: 6,403,085
Issued: Jun. 11, 2002
Appl. No.: 09/794,260
Filed: Feb. 27, 2001

U.S. Applications:

(63) Continuation-in-part of application No. 08/654,504, filed on May 28, 1996, now Pat. No. 6,254,864, which is a continuation of application No. 08/210,965, filed on Mar. 21, 1994, now Pat. No. 5,683,689, which is a continuation-in-part of application No. 07/999,185, filed on Dec. 30, 1992, now abandoned, which is a continuation of application No. 07/687,362, filed on Apr. 18, 1991, now abandoned, said application No. 08/210,965, is a continuation-in-part of application No. 07/999,186, filed on Dec. 30, 1992, now abandoned, which is a continuation of application No. 07/687,361, filed on Apr. 18, 1991, now abandoned.

(51) Int. Cl.
*A01N 69/00* (2006.01)

(52) U.S. Cl. ..... 424/93.5; 424/404; 424/405; 424/439; 424/442; 424/449; 424/493; 424/489; 435/254.1; 504/117

(58) Field of Classification Search ..... 435/254.1; 424/404, 405, 439, 442, 449, 493, 489, 93.5; 504/117
See application file for complete search history.

(56) References Cited

U.S. PATENT DOCUMENTS

| | | | |
|---|---|---|---|
| 4,925,663 | A | 5/1990 | Stimac |
| 4,992,275 | A | 2/1991 | Lush |
| 5,057,315 | A | 10/1991 | Gunner et al. |
| 5,057,316 | A | 10/1991 | Gunner et al. |
| 5,177,107 | A | 1/1993 | Meer et al. |
| 5,186,935 | A | 2/1993 | Tucker |
| 5,192,545 | A | 3/1993 | Nakashima |
| 6,254,864 | B1 * | 7/2001 | Stimac et al. |

FOREIGN PATENT DOCUMENTS

| | | |
|---|---|---|
| EP | 0190844 | 8/1996 |
| WO | 9010389 | 9/1990 |

OTHER PUBLICATIONS

Akre, R.D. et al. [1989] "Carpenter Ants: Their Biology and Control" *Ext. Bull. Washington State Univ. Coop. Ext. Serv.* EB 0818: 1–6.

Archbold, E.F. et al. [1986] "Characterization of a Yeast Infection in the German Cockroach (*Dictyoptera:Blattellidae*)" *Environ. Entomol.* 15:221–226.

Archbold, E.F. et al. [1987] Diagnosis of a Pathogenic Fungus (*Deuteromycotina:Hyphomycetes*) of German Cockroaches, Blattella Germanica (*Dictyoptera:Blattellidae*): *J. Med. Entomol.* 24:269–272.

Beatson, S.H. [1972] "Pharoah's Ants as Pathogen Vectors in Hospitals" *The Lancet* 1:425–427.

Brikman, L.I. et al. [1967] "Virulence of Entomopathogenic Spore–Forming Microorganisms in Relation to the Red House Ant, Monomorium pharaonis" Tr. Tsent. Nauch. – Issled. Dezinfek Inst. 18(2):70–77, abstract no 46398j in *Chemical Abstracts* 70(11):227.

Cochran, D.G. [1989] "Monitoring for Insecticide Resistance in Field–Collected Strains of the German Cockroach (*Dictyoptera:Blattellidae*)" *J. Econ. Entomol.* 35:336–341.

Coler, R.R. et al. [1984] "Effect of an Oothecal Parasitoid, *Comperia merceti* (Compare) (*Hymenoptera:Encyritidae*), on a Population of the Brownbanded Cockroach (*Orthoptera:Blattellidae*)" *Environ. Entomol.* 13:603–606.

Hagunbach, B.E. et al. [1989] "Bio. Con. Of the Amer. Cockroach (*Orthoptera:Blattidae*) w/Inundative Releases of *Tetrastichus hagenowil* (*Hymenoptera:Eulophidae*)" *J. Econ. Entomol.* 82:90–94.

Pereira et al. [1991] "Alginate and Cornstarch Mycelial Formulations of Entopahtogenic Fungi, *Beauveria bassiana* and *Metarhizum anisopliae*", J.Economic Entomology 84(6):1657–1661.

Rahmet–Alla, M., et al. [1989] "Studies on the Pathogenicity of Different Strains of *Bacillus cereus* for the Cockroach, *Leucophaea maderae" Journal of Invertebrate Pathology* 53:190–196.

Schal, C., et al. [1990] "Integrated Suppression of Synanthropic Cockroaches" *Ann. Rev. Entomol.* 35:521–551.

Thoms, E.M., et al. [1987] "Insecticide and Structural Modification Strategies for Management of Oriental Cockroach (*Orthoptera:Blattidae*) Populations" *J. Econ. Entomol.* 80:131–135.

Tsai, Y.H., et al. [1970] "Parasites of the German Cockroach (Blattella Germanica L) in New York City" *The Journal of Parasitology* 56(2):375–377.

Verratt, J.M. et al. [1987] "A Hemocoelic Candida Parasite of the American Cockroach (*Dictyoptera:Blattidae*)" *J. Economic Entomology* 80(6):1205–1212.

Zervos, S. [1983] "*Blatticola monandros* n.sp. (Nematoda: Thelastomatidae) from the Blattellid Cockroach *Parellipsidion pachycercum*" *New Zealand Journal of Zoology* 10:329–334.

* cited by examiner

*Primary Examiner*—Leon B. Lankford, Jr.
(74) *Attorney, Agent, or Firm*—Saliwanchik, Lloyd & Saliwanchik

(57) ABSTRACT

The subject invention concerns novel biopesticides and their use to control cockroaches, carpenter ants, and pharaoh ants. Specifically, highly virulent isolates of Beauveria bassiana in an agricultural composition, can be used to effectively control these pests. Exemplified are Beauveria bassiana No. 447, ATCC 20872, and Beauveria bassiana Sp111, ATCC 74038. Also described are unique formulations which are highly effective for delivering biocontrol agents to target pests. By using these novel compositions, target pests can be controlled without the environmental and public safety hazards presented by chemical control agents.

20 Claims, 11 Drawing Sheets

METHODS AND FORMULATIONS FOR CONTROL OF PESTS

Matter enclosed in heavy brackets [ ] appears in the original patent but forms no part of this reissue specification; matter printed in italics indicates the additions made by reissue.

CROSS REFERENCE TO RELATED APPLICATIONS

This application is a continuation-in-part of application Ser. No. 08/654,504, filed May 28, 1996, now U.S. Pat. No. 6,254,864 which is a continuation of application Ser. No. 08/210,965, filed Mar. 21, 1994, now U.S. Pat. No. 5,683,689 which is a continuation-in-part of application Ser. No. 07/999,185, filed Dec. 30, 1992, now abandoned; which is a continuation of application Ser. No. 07/687,362, filed Apr. 18, 1991, now abandoned. Application Ser. No. 08/210,965 is also a continuation-in-part of application Ser. No. 07/999,186, filed Dec. 30, 1992, now abandoned; which is a continuation of application Ser. No. 07/687,361, filed Apr. 18, 1991, now abandoned. The disclosures of each of these applications are hereby incorporated by reference in their entireties, including all figures, tables, and drawings.

BACKGROUND OF THE INVENTION

The development of biological control agents as alternatives to chemical insecticides for the control of important pest species is a subject of increasing interest. Concerns for the environment and exposure of man to harmful substances in air, food and water have stimulated legislation and restrictions regarding the use of chemical pesticides, particularly for pests found in the urban environment. Control of insect pests in urban areas is highly desirable but exposure to chemical pesticides in the household and from lawns and gardens is of great concern to the public. If given a choice, most people would use a non-toxic biological control rather than a toxic chemical to control insects in the urban environment. The problem is that very few biological alternatives to chemical insecticides are available for purchase and use by the public. For most insect pests that need to be controlled in the urban environment (ants, roaches, termites, fleas, wasps, etc.) there is no biological agent available for purchase as a product.

Cockroaches are serious economic pests in urban areas. Because cockroaches are so closely associated with humans and commonly feed on decaying food, crumbs, or scraps, and frequent unsanitary areas such as sewage systems and septic tanks, their presence leads to suspicion of a threat to human health. Pathogenic organisms have been isolated from cockroaches collected in domestic or peridomestic environments; however, the role of cockroaches as vectors of pathogens is controversial. Unlike many blood-feeding arthropods whose feeding behavior results in the direct transmission of pathogens to humans, cockroaches have the potential to transmit pathogens indirectly via contamination of foods or utensils used to prepare food. It has been demonstrated that cockroaches acquire pathogenic bacteria simply by walking over cultures and showed that these pathogens are subsequently transferred to foodstuffs via the normal foraging behavior of the infested cockroaches. Aside from bacterially caused food poisoning and diseases such as typhoid and dysentery, many other human illnesses and diseases associated with microorganisms isolated from cockroaches have been reported. These include paralytic polio, giardiasis, otomycosis, pneumomycosis, and various worms such as hookworm and tapeworm.

Besides the possible role of cockroaches as vectors of pathogenic microorganisms, the mere presence of these insects is known to contribute to human morbidity in other ways. Perhaps the most insidious aspect is the psychological impact of these pests in terms of the anxiety and stress related to infestation, which in some instances can take on pathologic dimensions. Further, defensive secretions among cockroach species may cause burning sensations, vertigo, or nausea in individuals who come into contact with the insects.

Current cockroach control methods in buildings include preventative and corrective approaches. Preventative measures emphasize sanitation to eliminate harborages and food sources, sealing off access routes, and the creation of inhospitable environments by the application of boric acid or sorptive dusts in wall voids during construction (Ebeling, W. [1971] Ann. Rev. Entomol. 16:123–158; Ebeling, W. [1978] Urban Entomology, Berkeley: Univ. Calif. Div. Agric. Sci. 695 pp.). However the implementation of these measures is difficult and thus limits their effectiveness (Thoms, E. M., W. H. Robinson [1987] J. Econ. Entomol. 80:131–135). Corrective measures used to suppress established infestations emphasize the use of insecticide applications. A commonly used technique is to spray insecticides with long residual activity in areas frequented by cockroaches at fixed time intervals (Schal, C., R. L. Hamilton [1990] Ann. Rev. Entomol. 35:521–551). Despite short term suppression of cockroach populations, toxic residues and the development of insecticide resistance (Cochran, D. G. [1989] J. Econ. Entomol. 82:336–341) make total reliance on this technique undesirable. Alternative corrective measures such as the placement of toxic bait traps may provide sufficient control under proper conditions (Thoms & Robinson [1987], supra).

The use of natural enemies for the biological control of cockroaches has been examined to varying degrees. Although traps using biocontrol agents have been proposed, these traps are only as good as the biocontrol agent used. U.S. Pat. Nos. 5,057,315 and 5,057,316. Field releases of parasitoids of the American and brown banded cockroaches resulted in rates of parasitism as high as 95% and has generated some optimism for their potential utilization (Coler, R. R., Van Driesche, R. G., Elkinton, J. S. [1984] Environ. Entomol. 13:603–606; Hagenbuch, B. E., R. S. Patterson, P. G. Koehler [1989] J. Econ. Entomol. 82:90–94). Pathogenic yeasts isolated from laboratory cockroach colonies also have been suggested as possible biological control agents, but more research is required to evaluate their potential (Archbold, E. F., M. K. Rust, D. A. Reierson [1987] J. Med. Entomol. 24:269–272; Archbold, E. F., M. K. Rust, D. A. Reierson, K. D. Atkinson [1986] Environ. Entomol. 15:221–226; Verrett, J. M., K. B. Green, L. M. Gamble, F. C. Crochen [1987] J. Econ. Entomol. 80:1205–1212). Numerous other fungi, bacteria, protozoans, and nematodes have been reported to be associated with cockroaches, but their potential as biological control agents is not significant, or has not been fully evaluated (Roth and Willis [1960] Smithsonian Misc. Coll. Vol. 141; Tsai, Y. H., K. M. Cahill [1970] J. Parasitol. 56:375–377; Zervos, S. [1983] N. Z. J. Zool. 10:329–334; Rahmet-Alla, M., A. F. Rowley [1989] J. Invert. Path. 53:190–196). Thus, there is a significant and long-felt need for a more effective and safe means for controlling cockroaches.

Carpenter ants, Camponotus spp., are distributed throughout North America. Some of the more common and/or studied species include C. modoc in the Pacific northwest, C. clarithorax in southern California, and the C. floridanus in Florida. C. pennsylvanicus, C. noveboracensis,and C.

abdominalis, are found in the east (Ebeling, W. [1978] Urban Entomology, Univ. Calif.: Berkeley p. 209–213). Public concern over carpenter ants has been increasing due to the greater probability of structural infestations as suburban developments extend into the forest habitats of the ants.

Pestiferous species of carpenter ants may be considered nuisance pests because of their foraging activity inside homes. More significant damage occurs when carpenter ants extend their nests into sound wood. Nesting sites may be located in live and dead trees, sometimes resulting in damage to shade trees. Nests may also be established in walls and support beams of structures, or in voids within doors, walls, and furniture. Preference for moist or decaying wood has been reported, but nesting sites are not restricted to such areas. Carpenter ant populations develop relatively slowly with colonies of 300–2,000 workers being produced over a 2-year or longer period for various species. The presence of reproductives follows this slow development since their production has been reported only from well established colonies (Hansen, L. D., R. D. Akre [1985] Biology of carpenter ants in Washington state (Hymenoptera: Formicidae: Camponotus), Melanderia 43: 62 pp.; Pricer J. L. [1908] Biol. Bull. 14:177–218). Despite the slow colony growth, large colonies with satellites colonies have been found. Worker movement occurs between the main colony and the satellites, which serve as areas for further brood development and colony expansion (Hansen and Akre [1985], supra).

Current methods for controlling structural infestations of carpenter ants include sanitation of potential and current nest sites, minimizing access to structures (eg. preventing the contact of tree branches with a structure), and the application of insecticides to repel (perimeter spray barriers) and/or eliminate carpenter ants. The use of boric acid dust in dry, wall voids is reported to be effective for up to 20 years (Hansen and Akre, supra).

Recommendations for the chemical control of established structural infestations in the home are often accompanied with warnings of possible hazards to the applicator as well as children and pets. Alternative control methods such as effective biological control agents have not been found (Akre, R. D., L. D. Hansen, A. L. Antonelli [1989] Ext. Bull. Washington State Univ. Coop. Ext. Serv. 1989 rev. no. EB 0818, 6 pp.). A need clearly exists for a safe, effective biological control agent for carpenter ants.

Pharaoh ants, Monomorium pharaonis, have been described as the most persistent and difficult of all our house-infesting ants to control or eradicate (Smith, M. R. [1965] USDA-ARS Tech. Bull. No. 1326, 105 pp.). It is a tropical species which has extended its range to more temperature regions by establishing colonies in heated buildings. Pharaoh ants frequently infests buildings where food is prepared, and have been found to carry pathogenic organisms (Beatson, S. H. [1972] Lancet 1:425–427).

The difficulty in controlling pharaoh ants may be attributed to their inaccessible nesting sites, rapid population growth, and dispersion of colonies. Their small size allows establishment of colonies in any suitable location, including unusual places such as between books and in stored clothing. With multiple queen colonies, and the warm (30° C.), humid (63–80% RH) conditions that favor pharaoh ants, large colonies can develop rapidly. Portions of these large colonies may disperse to form new colonies at any time, probably in response to overcrowding and unfavorable microenvironmental conditions. Unlike other ant species, pharaoh ants do not exhibit intercolony aggression. This permits the adoption of ants from other colonies and may further enhance the establishment of new colonies and reinfestations. Pharaoh ants also forage for food more than 35 m from the nest without distinct trail following, and thus make nests difficult to find and eradicate.

Control methods for pharaoh ants emphasize the use of insect growth regulators (IGR) or toxicants incorporated into baits. Properly implemented bait programs are effective, however it may take over a month to achieve control. Insecticide applications, while fast acting, usually do not eliminate colonies, and may be unacceptable in certain areas where toxic residues are a concern. In addition, insecticide applications are generally not compatible with bait programs. A need exists for safe and effective biological control agents for pharaoh ants.

A United States patent has been granted for a fungus showing high activity against fire ants, U.S. Pat. No. 4,925,663. This isolate, designated Beauveria bassiana isolate No. 447, was deposited in a public repository. No biological activity other than the activity against fire ants had been previously reported for this isolate, nor could activity against other pests be inferred from the mere knowledge that the isolate was active against fire ants. The subject invention concerns the new uses of B. bassiana No. 447.

BRIEF SUMMARY OF THE INVENTION

The subject invention concerns the use of highly virulent Beauveria bassiana isolates to control certain pests, including cockroaches, carpenter ants, fire ants, and pharaoh ants. Specifically exemplified herein are formulations containing B. bassiana isolates No. 447 and SP111. These isolates, advantageously, show unexpectedly high virulence against certain pests, including cockroaches, carpenter ants, fire ants, and pharaoh ants, and do not produce the environmental hazards associated with chemical control agents. The fungal biopesticides described herein can be applied to each of these pests in any of their normal habitats. The fungus may be applied, for example, directly to the pests, in trays, or applied to their surroundings, or anywhere that these pests are a problem. The subject invention also includes mutants of the exemplified isolates which substantially retain the high virulence of the parent strain.

A further aspect of the subject invention concerns unique formulations which can be used to effectively deliver biocontrol agents to target pests. In a preferred embodiment a biocontrol agent is delivered in a formulation which is readily foraged by the target pest and adheres to the body of the pest. Specifically exemplified herein is a formulation which has been discovered to be non-repulsive to fire ants and other pests. This discovery is quite unexpected because pests are known to be repelled by many formulations of microbial agents. The formulation of the subject invention is particularly advantageous because it has been found to be highly effective in delivering the biocontrol agent to the target pest. The formulation of the subject invention comprises a unique blend of a food source and the fungal biocontrol agent. In a preferred embodiment, a drying agent is also used. These ingredients are presented as a dry powder.

DETAILED DESCRIPTION

Figure 1:
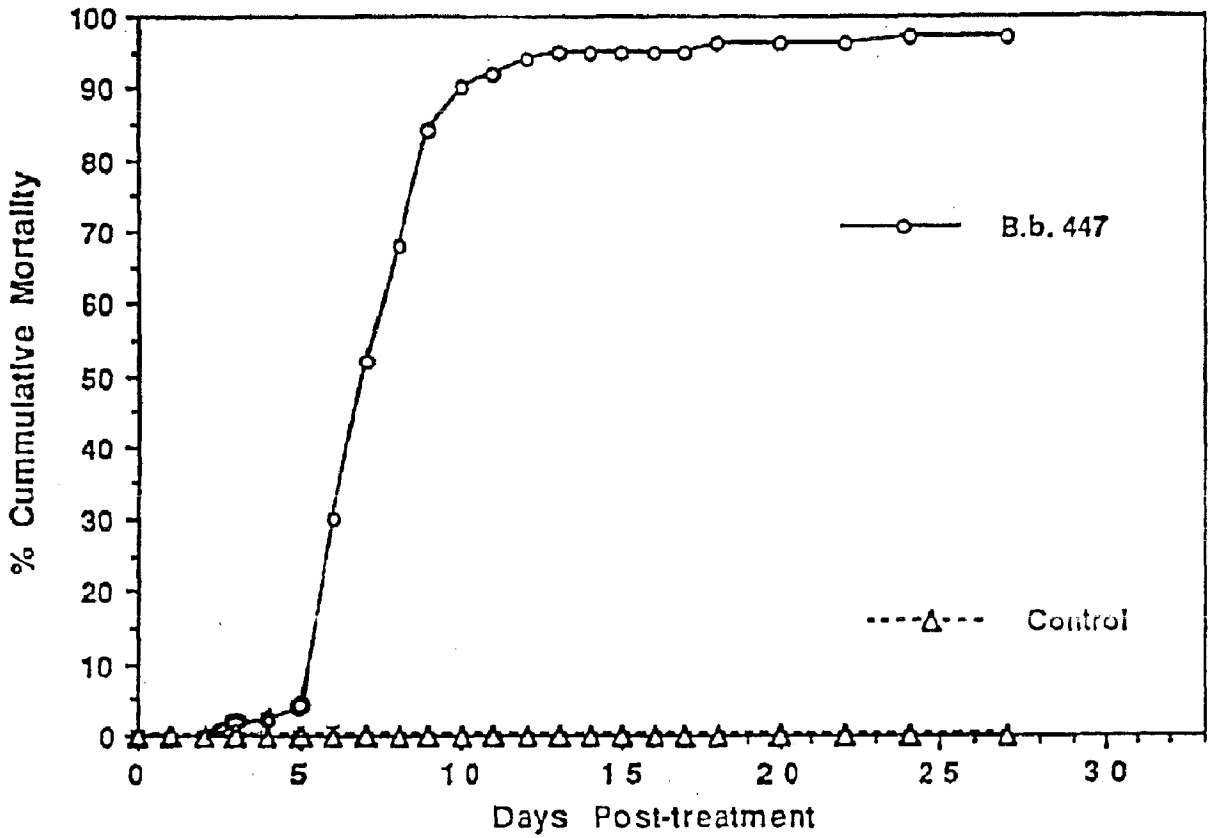
FIG. 1 shows cumulative percent mortality of carpenter ants exposed to B. bassiana isolate No. 447.

The subject invention concerns the use of fungal biocontrol agents to control certain pests. Specifically exemplified herein is the use of Beauveria bassiana isolates No. 447 and SP111. B. bassiana SP111 is a novel isolate. A further aspect of the subject invention includes formulations which are highly effective in delivering the biocontrol agent to the target pest.

Biologically pure cultures of Beauveria bassiana No. 447 and Beauveria bassiana SP111, have been deposited in the American Type Culture Collection (ATCC), 10801 University Boulevard, Manassas, Va. 20110-2209. The deposit information and accession numbers are as follows:

| CULTURE | ACCESSION NUMBER | DEPOSIT DATE |
|---|---|---|
| *Beauveria bassiana* Isolate No. 447 | ATCC 20872 | Dec. 29, 1987 |
| *Beauveria bassiana* Isolate No. SP111 | ATCC 74308 | Mar. 5, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository by unable to furnish a sample when requested, due to the condition of a deposit. All restrictions on the availability to the public of the subject culture deposits will be irrevocably removed upon the granting of a patent disclosing them.

The entomopathogenic fungus Beauveria bassiana is an imperfect fungus (Fungi Imperfecti) in the subdivision Deuteromycotonia. The genus Beauveria Vuill is within the Class Deuteromycetes and is distinguished from other genera by having conidia that are borne singly, not catenulate and having the fertile portion of the conidiophore zig-zag in shape and drawn out at the tip. The species Beauveria bassiana has spherical, not ellipsoid, conidia measuring 2–3 $\mu$m by 2–2.5 $\mu$m and with conidiophores forming dense bunches.

For a biological control agent to be effective at a practical level to control cockroaches, carpenter ants, and pharaoh ants, it is essential that the agent not only exhibit pathogenicity against these pests, but it must also be virulent. The more virulent it is, the better it is as a biocontrol agent. Though some fungal isolates have been shown to have some pathogenicity to these pests, these isolates did not have the essential virulence to function as a biocontrol agent. There is no known way to convert a pathogenic non-virulent fungal isolate into a pathogenic virulent isolate. Thus, the discovery of the novel isolate of the invention accomplishes a goal which has long been sought after.

Mode of action and virulence. Like most entomogenous fungi, Beauveria bassiana initiates infection by a germinating spore (conidium) attaching to and subsequently penetrating the cuticle of the insect host. Advantageously, and unexpectedly, the claimed Beauveria bassiana isolates attach very securely to the cuticle of cockroaches and ants and are typically not removed by the insect's grooming activities. This may account somewhat for the high virulence of the fungus. As the fungus penetrates the insect's cuticle, the invasive hyphae begin to enter the host's tissues and ramify through the hemocoel. Hyphal bodies or segments of the hyphae distribute throughout the hemocoel, filling the dying insect with mycelia. Emergence hyphae grow out through the insect's integument and produce spores on the external surface of the host. These spores, or conidia, are dispersed and capable of infecting new host insects. B. bassiana spores can be dispersed within the nest by the activities of the pests.

Formulations. The formulations of the subject invention were found to be particularly effective for the control of fire ants and other pests. In a preferred embodiment, the formulation comprises a dry powder having the fungal biocontrol agent and a food component. Preferably, the formulation further comprises a drying agent. Optionally, the formulation may also comprise an attractant. The preferred formulation is non-repellant and includes a food source so that the target pest will forage and recruit other nestmates for foraging activity. Furthermore, the formulation of the subject invention has been found to advantageously adhere to the body of the target pest, thereby facilitating colonization of the pest by the fungal biocontrol agent. The ability to adhere to the pest makes the formulation of the subject invention quite distinct from other formulations which are currently used to administer chemical pesticides.

Drying agents useful in the practice of the claimed invention include chemically acting drying agents and physically acting drying agents. Various combinations of one or more chemically acting and/or physically acting drying agents may be used in the practice of the invention. Chemically acting drying agents bind the water in the form of crystallization. Examples of these types of drying agents are calcium chloride, sodium sulfate, or magnesium perchlorate. Other chemically acting drying agents react with water and include phosphorus pentoxide, sicacide, metals, and metal hydrides.

Physically acting drying agents are substances that adsorb water on the surface and in the pores of the drying agent.

Examples of these types of drying agents are t.h.e.™ Desiccant ($SiO_2$, EM Science, Inc., Gibbstown, N.J.), synthetic and naturally occurring zeolites, and aluminum oxide (alumina). Drierite (calcium sulfate), calcium chloride, calcium oxides, sodium sulfate, copper (II) sulfate, potassium carbonate, and magnesium oxide may also be used as drying agents.

In one embodiment, the formulation of the subject invention consists of about 25–40% peanut material, about 45–60% cornstarch, about 2–20% fungal biocontrol agent, and about 0–15% drying agent. In a specific embodiment, the formulation can comprise about 35% peanut material, about 50% cornstarch, about 5% drying agent, and about 10% fungus. The drying agent can be any one of many materials known to those skilled in the art which are small particles but have a high surface area to volume ratio so as to effectively remove water or oils from the formulation to create a dry powder. Preferably, the drying agent can be diatomaceous earth or a synthetic calcium silicate such as Micro-Cel™.

The peanut component of the formulation is preferably prepared by grinding roasted peanuts so as to obtain a powder. To achieve a dry powder, it is best to grind the peanuts together with the cornstarch and/or a drying agent. Preferably, the components of the formulation are small particles and will pass through a 60 mesh sieve. Typically, the cornstarch and drying agent will pass through a much smaller sieve, such as at 300 mesh. Preferably, the formulation is a powder which is free flowing and does not stick together in clumps. Food sources other than peanut material or cornstarch can also be used according to the subject invention. The choice of a food source will depend upon the particular pest which is the target for control. Also, various attractants known to those skilled in the art can be used. These attractants can be, for example, pheromones or various extracts. In a preferred embodiment, the fungal pathogen is B. bassiana No. 447 or B. bassiana SP111. However, other microbes can be used as can other biocontrol agents. For example, Bacillus thuringiensis can also be used with the formulation of the subject invention.

To evaluate the control achieved using the materials and methods of the subject invention, tests were conducted to compare the control of pests achieved with certain commercial pesticides. As described below, these tests demonstrated that the fungal formulations of the present invention are highly effective in controlling pests.

Following are examples which illustrate procedures, including the best mode, for practicing the invention. These examples should not be construed as limiting. All percentages are by weight and all solvent mixture proportions are by volume unless otherwise noted.

EXAMPLE 1

Preparation of the Fungus

The subject fungus can be produced in trays with a rice-based medium. An isolate of fungal inoculum is used to initiate the growth of the fungus in the trays. The initial inoculum is prepared in petri dishes. The pure spores are then transferred into jars containing sterile white rice without skins. The medium for the trays is prepared as follows:

1. The rice is pre-cooked for 10 minutes.

2. 750 grams of cooked rice is placed in polyethylene bags and sterilized in an autoclave at 120° C. for 30 minutes.

3. Within a laminar flow hood, one teaspoon of spores and rice from the inoculum jars is added to each bag of prepared sterile medium.

4. Each bag is closed tightly by folding and stapling the open end. 5. The bags are transferred to a sterile room with positive pressure, temperature at 25.0–27.0° C., relative humidity above 70%, and 16 hours photophase. This room is known as the environment room.

After 3 days in the environment room, bags containing mycelia are selected and their contents are transferred to plastic trays. The size of the trays is such that each tray will accommodate the contents of 2–3 bags. The trays and their contents are left in the environment room for 12–15 days. At the end of the 12–15 day period, the trays are transferred to a room with a cool (10–20° C.) current of clean air. The trays are left in this room until the cool air has dried the rice and fungus mixture.

The uncontaminated trays of rice covered with fungus can be harvested and prepared for application or storage. If the fungus will be applied to cockroaches or ants within 1–2 weeks after production, conidia can be collected by shaking and sieving. The resulting powder contains spores and some mycelia, and can be applied directly to target insects or used to prepare a formulation as a liquid, powder, or bait.

If the fungus is to be stored, the mixture can be mixed with cornstarch or talc and placed into sterile plastic containers sealed tightly and stored in a refrigerator at 4° C. or in a room with a temperature range of 10–25° C. and no direct sunlight. The high virulence of B. bassiana can be compromised by bacterial or fungal contamination. Therefore, throughout the preparation of the fungus, great care must be taken to maintain the sterility of all instruments and equipment.

As the following examples demonstrate, the fungus-containing product can be applied to target pests and their nests as a liquid, powder, or put out as a baited trap for the pests to forage, become infected, and carry inoculum back to the nest.

EXAMPLE 2

Spray Application

Spraying can be used for treating individual ants or cockroaches or small groups of these pests. A fungal suspension containing $1.0\times10^7$ to $1.0\times10^9$ spores per milliliter of water can be sprayed on the target pests using an airbrush or other means as an applicator

EXAMPLE 3

Powder Application

A fungal spore and mycelia mixture can be mixed with cornstarch or talc and applied to the pests' surroundings as a dry powder.

The powder is prepared as in Example 1 above. The sieved B. bassiana powder which contains the rice, spores, and mycelia is mixed with cornstarch or talc. Application of this powder to the nests or directly to the pests can facilitate rapid and widespread fungal growth within the nest or on the pest.

The application can be accomplished using an pressurized air applicator with an attachment that distributes the mixtures into cracks and crevices of a pest-inhabited building. During and following application, pests covered with white powder will be observed. These infected pests will die within 1–5 days, and the spores they produce will be infective to other pests. There should be a marked decrease in activity within 1–3 days and death should occur within 1–2 weeks following application. Active spores will remain in the surroundings at the nest site, thereby providing inoculum to infect other roaches or ants.

EXAMPLE 4

Baited Trap Application

The fungal powder can be used in a trap in which entryways are laced with fungal inoculum. Preferably, fungal spores are utilized. A bait attractant contained within the trap will be foraged by cockroaches or ants and the foragers will become infected. These infected individuals will return to the nest contaminated and thereby introduce the fungal disease into the nest. A vegetable oil or other liquid substance can be added to a bait in the trap to make it more attractive to the pests. Various attractants, including pheromone compounds, are well known to those skilled in this art. The baited traps should be placed in cabinets, along baseboards, windowsills, etc. A quantity of 0.5–2.0 grams of fungal mixture containing spores and mycelia should be contained in each trap. The number of traps used in an area will depend on the level of infestation.

EXAMPLE 5

Treatment of Carpenter Ants with B. bassiana No. 447

Carpenter ants (Camponotus floridanus), were exposed Beauveria bassiana No. 447. Each treatment entailed exposing two groups of 50 ants each to conidia of the isolates. Ants were coated with a conidia/cornstarch mixture, by gently shaking the ants and spores together in a covered container. The control treatment consisted of cornstarch only. Ants were subsequently held in open plastic boxes that contained a nest cell (100 mm covered petri disk with the bottom dish filled with plaster that was periodically moistened with water) and honey water for food.

Mortality was recorded daily for 18 days beginning with the second day after exposure. The test was terminated after 28 days. Dead ants were individually held under high humidity and examined for sporulation to determine infection rates.

Carpenter ants exposed to isolates of B. bassiana sustained over 95% mortality (FIG. 1). At least 49% of the dead ants developed sporulating bodies of the fungi to which they were exposed, indicating that these isolates can grow and reproduce on carpenter ants.

EXAMPLE 6

Treatment of Carpenter Ants with B. bassiana SP111

Carpenter ants (Camponotus floridanus), were exposed Beauveria bassiana SP111. Each treatment entailed exposing two groups of 50 ants each to conidia of the isolates. Ants were coated with a conidia/cornstarch mixture, by gently shaking the ants and spores together in a covered container. The control treatment consisted of cornstarch only. Ants were subsequently held in open plastic boxes that contained a nest cell (100 mm covered petri dish with the bottom dish filled with plaster that was periodically moistened with water) and honey water for food.

Mortality was recorded daily for 18 days beginning with the second day after exposure. The test was terminated after 28 days. Dead ants were individually held under high humidity and examined for sporulation to determine infection rates.

Figure 2:
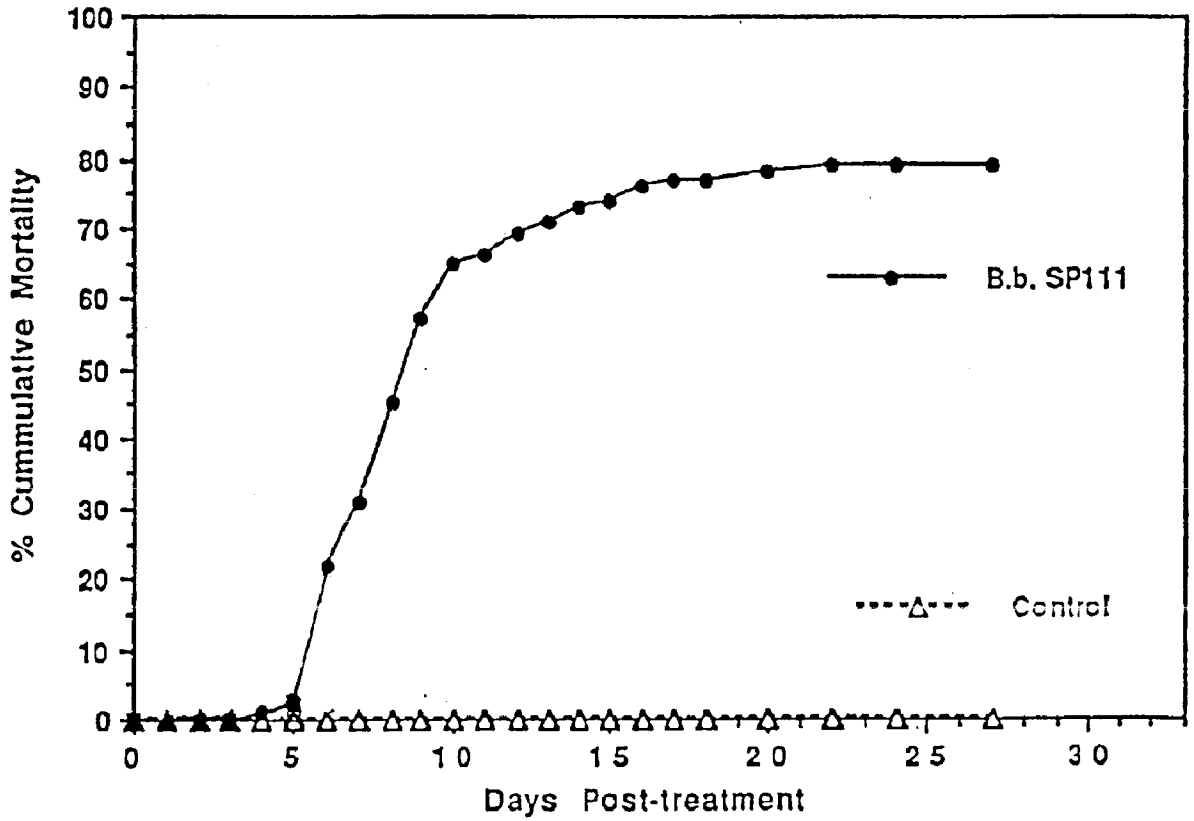
FIG. 2 shows cumulative percent mortality of carpenter ants exposed to B. bassiana isolate SP111.

Carpenter ants exposed to B. bassiana SP111 sustained over 75% mortality (FIG. 2). At least 49% of the dead ants developed sporulating bodies of the fungi they were exposed to, indicating that these isolates can grow and produce spores on carpenter ants.

EXAMPLE 7

Treatment of Pharaoh Ants with B. bassiana No. 447

Pharaoh ants were exposed to a mixture comprising B. bassiana No. 447 conidia as the active ingredient. Three colonies of approximately 100–200 ants were individually dusted with the conidia in a petri dish and allowed to crawl out into a nest cell (15×40 mm plastic petri dish with a plaster filled base and entrance holes in the lid). Controls consisting of three colonies were not dusted. The ant colonies were held separately in larger petri dishes along with the nest cells and honey water. Mortality was recorded daily for 25 days. Dead ants were individually surface sterilized and held under high humidity to the rate of infection.

Figure 3:
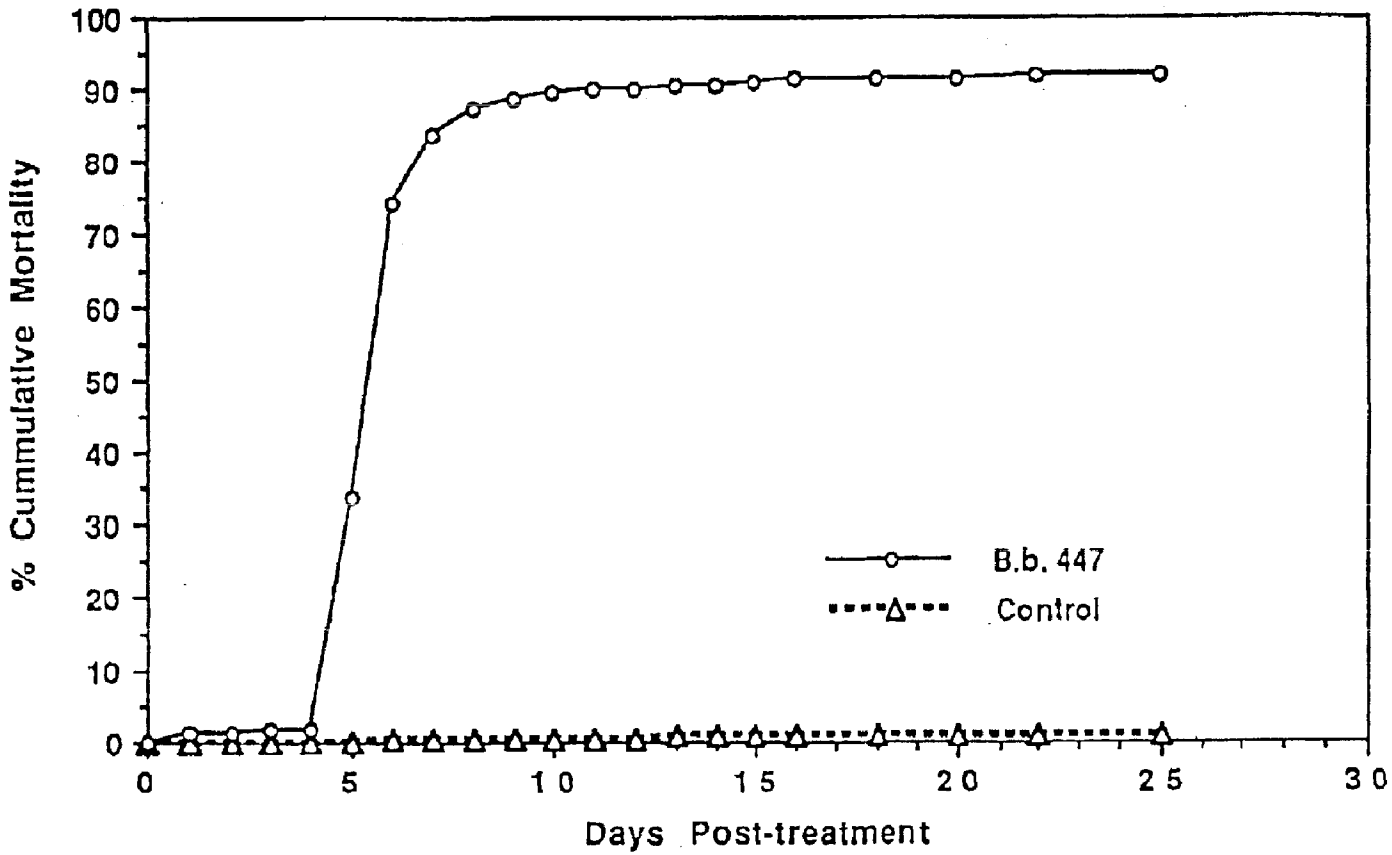
FIG. 3 shows cumulative percent mortality of pharaoh ants exposed to B. bassiana isolate No. 447.

Pharaoh ant exposure to B. bassiana 447 resulted in 90% mortality after 8 days (FIG. 3). Furthermore, all of the dead ants were confirmed to have fungal spores, indicating that the fungus can successfully develop on pharaoh ants.

EXAMPLE 8

Treatment of Cockroaches with B. bassiana No. 447

For the German cockroach, Blattella germanica, B. bassiana No. 447 was tested for ability of its conidia to infect and kill the host. Groups of 50 male cockroaches were anesthetized with $CO_2$ and then dusted with conidia, within a covered container (8 oz). Controls consisted of a group of 20 cockroaches. Dusted cockroaches were transferred individually into separate petri dishes (10×35 mm) containing moistened filter paper. Mortality was recorded from the second day after conidia application and daily thereafter. Dead cockroaches were individually held in a humidity chamber for 10 days to identify sporulating fungi.

For the American cockroach, Periplaneta americana, B. bassiana No. 447 was applied by brushing the conidia onto anesthetized cockroaches. Cockroaches were then held in petri dishes as described above, at 26° C.

Figure 4:
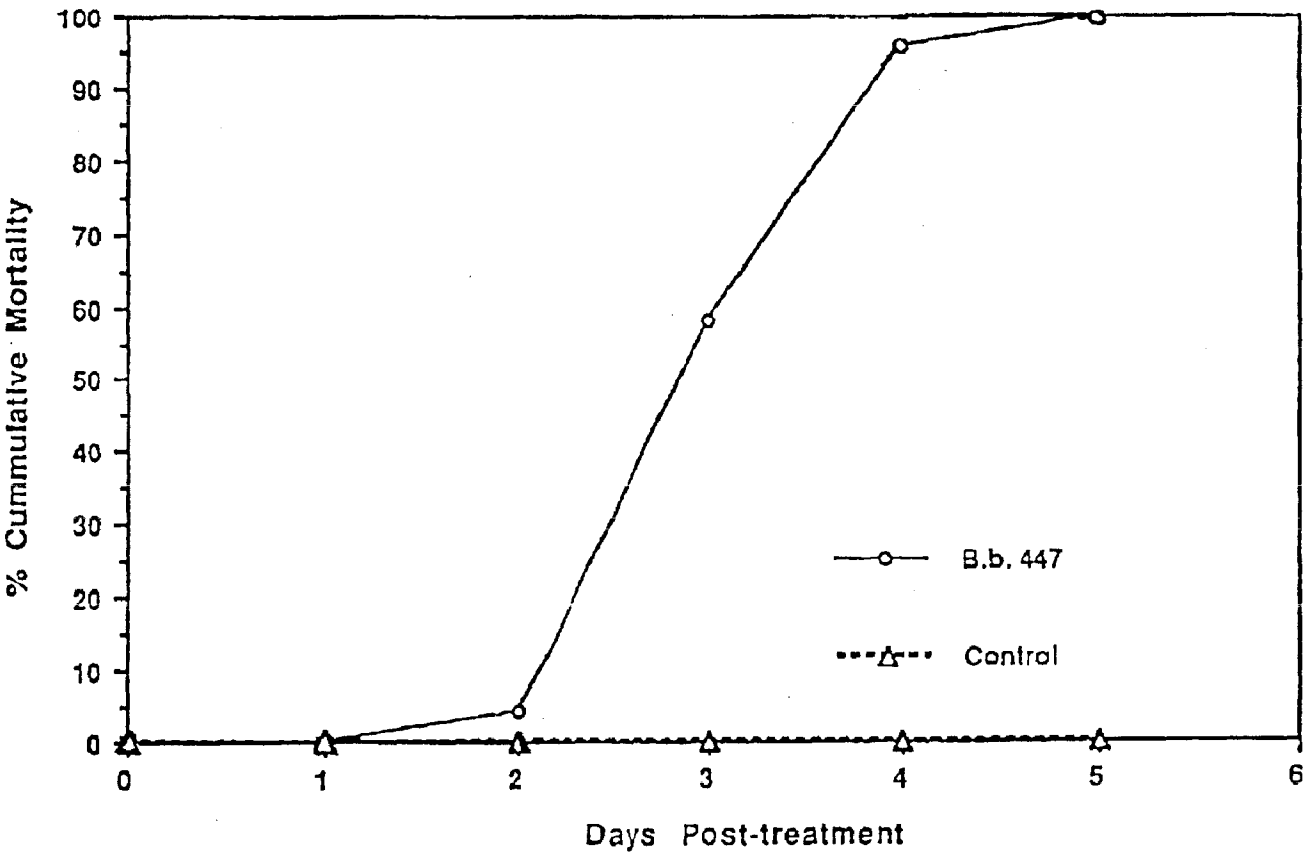
FIG. 4 shows cumulative percent mortality of German cockroaches exposed to B. bassiana isolate No. 447.

In the test with German cockroaches the fungal isolate B. bassiana No. 447 (FIG. 4) caused 100% mortality after contact with spores. Sporulation of the fungus was evident on 82% of the dead cockroaches.

Figure 5:
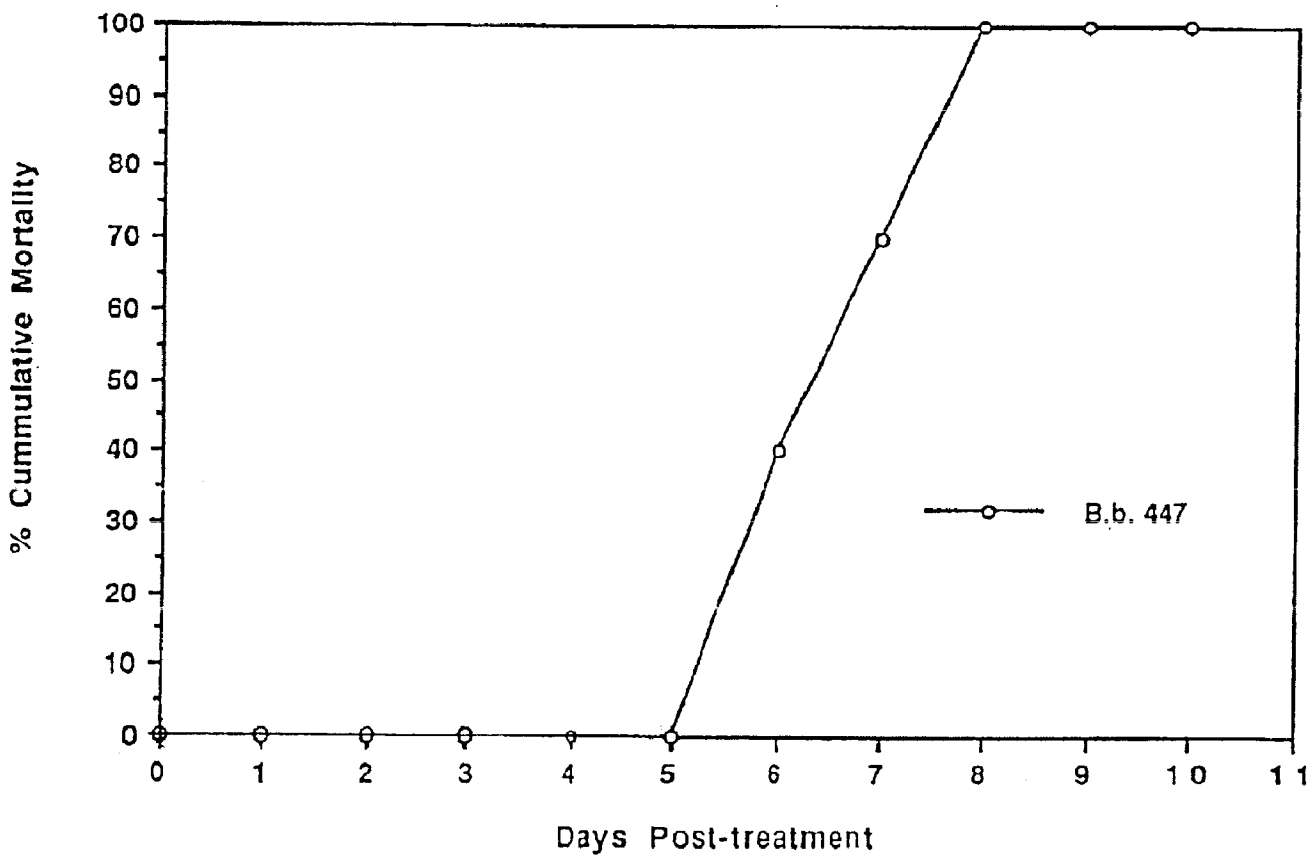
FIG. 5 shows cumulative percent mortality of American cockroaches exposed to B. bassiana isolate No. 447.

For the exposures of the American cockroaches, the B. bassiana isolate caused 90% or more mortality after 8 days (FIG. 5). Fungal sporulation occurred on all of the dead American cockroaches.

EXAMPLE 9

Treatment of Cockroaches with B. bassiana SP111

For the German cockroach, Blattella germanica, B. bassiana SP111 was tested for ability of its conidia to infect and kill the host. Groups of 50 male cockroaches were dusted with conidia, within a covered container (8 oz). Controls consisted of a group of 20 cockroaches. After exposure to conidia, cockroaches were anesthetized with $CO_2$ and transferred individually into separate petri dishes (10×35 mm) containing moistened filter paper. Mortality was recorded beginning on the second day after conidia application and daily thereafter. Dead cockroaches were individually held in a humidity chamber for 10 days to identify sporulating fungi.

Figure 6:
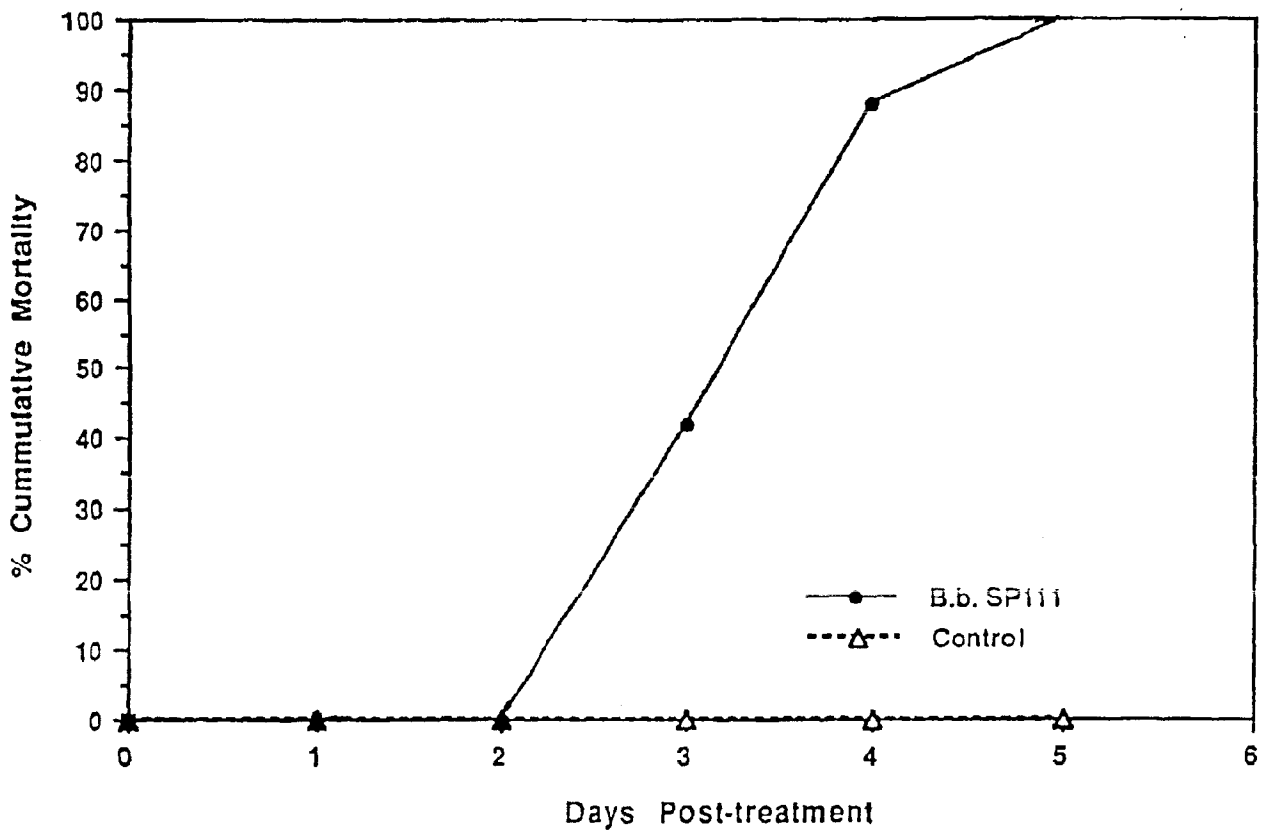
FIG. 6 shows cumulative percent mortality of German cockroaches exposed to B. bassiana isolate SP111.

In the test with German cockroaches the fungal isolate B. bassiana SP111 (FIG. 6) caused 100% mortality after contact with spores. Sporulation of the fungus was evident on about 82% of the dead cockroaches.

EXAMPLE 10

Evaluation of B. bassiana Bait Formulations for Control of Fire Ants

Bait formulations with ground peanut material were offered to colonies of fire ant workers in plastic boxes (≈20×12×10 cm) containing a small dish of water and a plastic petri dish (60 mm diameter) to serve as a nest cell. Colonies were established 2–4 days before the start of the experiment to allow ants to adapt to their new environment. The formulations (0.5 g) were offered on weigh papers (1 square inch) or small dishes and left in the boxes for 3–4 days. Two controls were used: a clean control which received no formulation but only water, and a bait control which received the bait formulation without any fungus. Abbott-corrected mortality greater than 70% at 14 days after treatment was observed for the fungal isolate containing about 10% of the B. bassiana No. 447.

EXAMPLE 11

Figure 7:
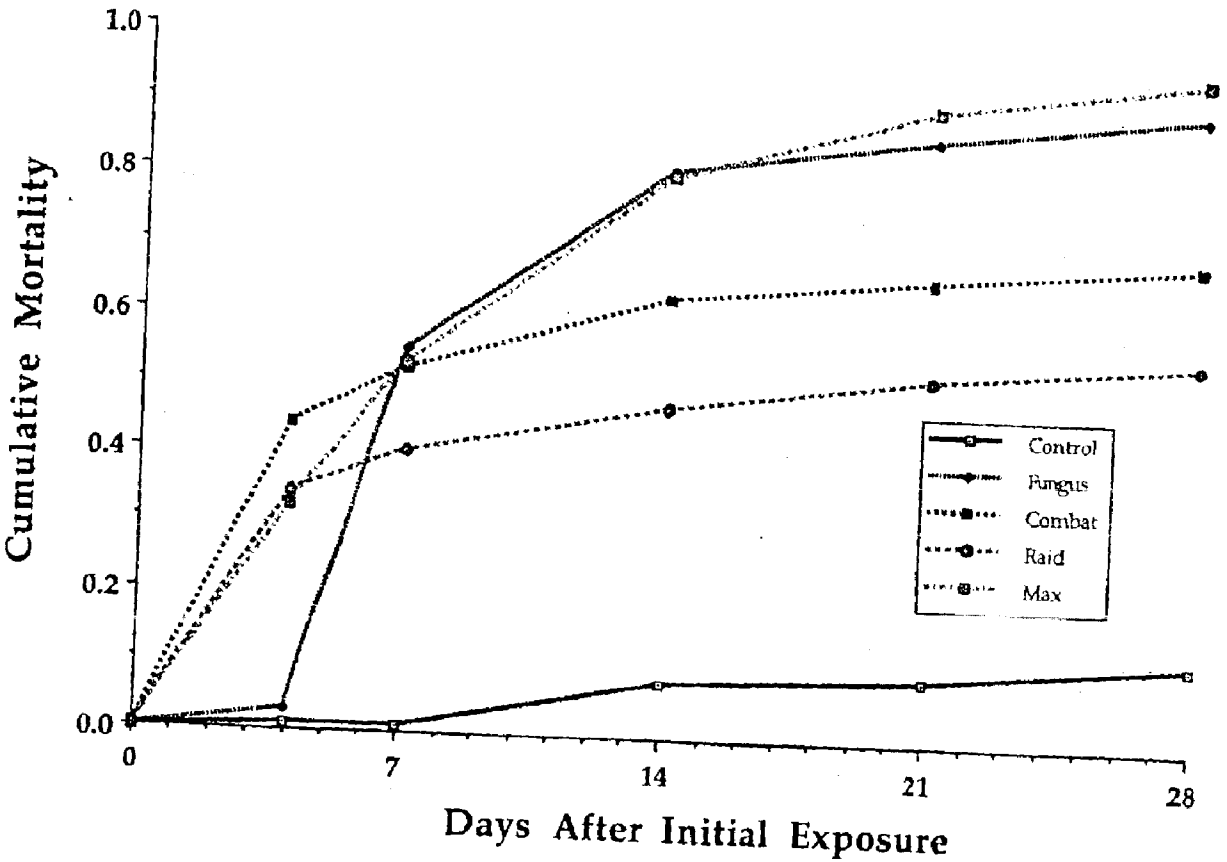
FIG. 7 shows mortality of fire ants from the fungal formulation in comparison to chemicals for commercial traps.

Chemical Baits from Traps Compared to Fungal Formulations for the Control of Fire Ants The chemical baits which were compared are from: MAX ant trap, RAID ant trap, and COMBAT ant trap. The chemical baits were removed from the traps and offered to ants on paper. The control received the same formulation as the fungus treatment but without conidia. The fungal formulation contained peanut material and cornstarch and 10% conidia of B. bassiana No. 447. MAX and the fungal formulations had similar mortality, although MAX caused mortality to increase much more rapidly than the fungus as expected, since the fungus requires 3–4 days to infect and kill the insect. As shown in FIG. 7, COMBAT and RAID were less efficient than MAX and Beauveria bassiana.

EXAMPLE 12

Figure 8:
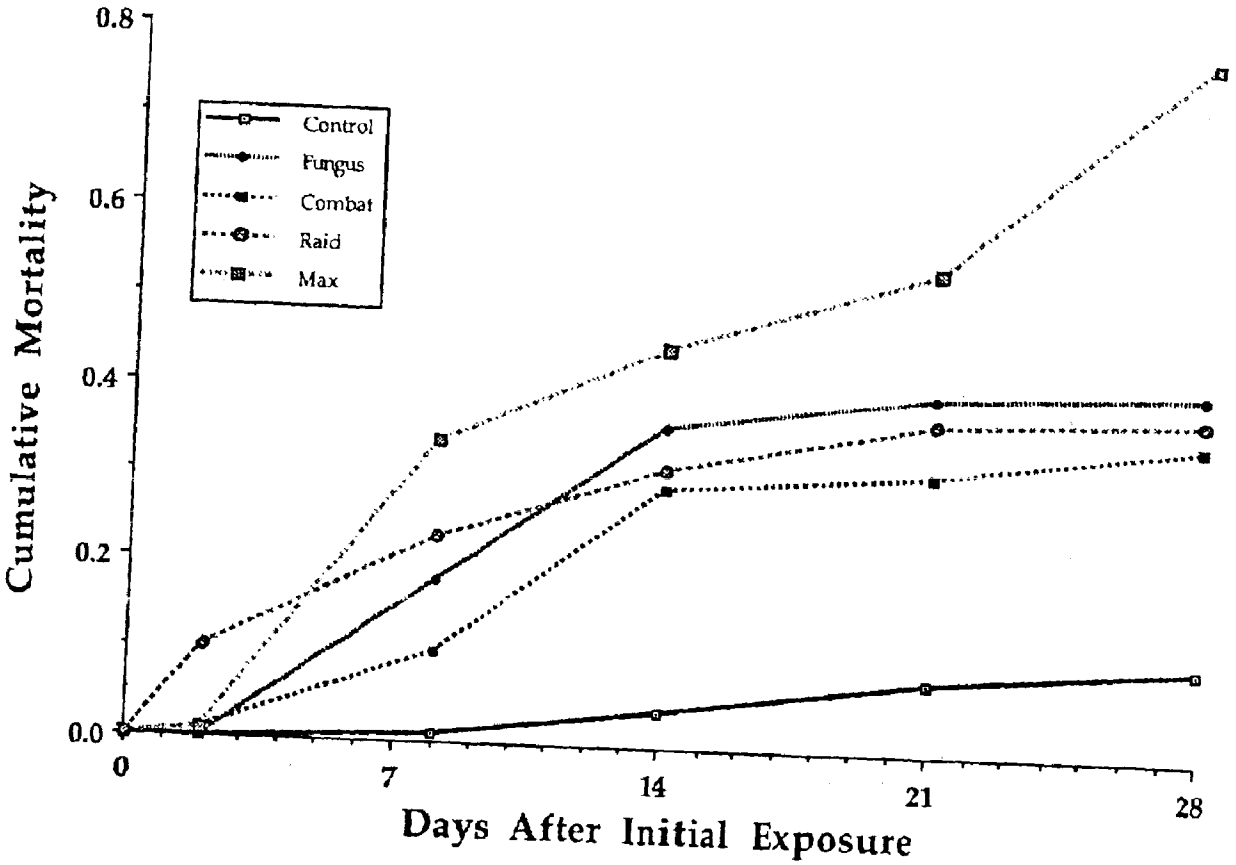
FIG. 8 shows a comparison of chemical baits from traps to fungus formulation for the control of pharaoh ants.

Chemical Baits from Traps Compared to Fungal Formulation for the Control of Pharaoh Ants The chemical baits which were compared are from: MAX ant trap, RAID ant trap, and COMBAT ant trap. The chemical baits were removed from the traps and offered to ants on paper. The control received the same formulations as the fungus treatment but without conidia. The fungal formulation contained peanut material and cornstarch and 10% conidia of B. bassiana No. 447. The results of this experiment is shown in FIG. 8.

EXAMPLE 13

Figure 9:
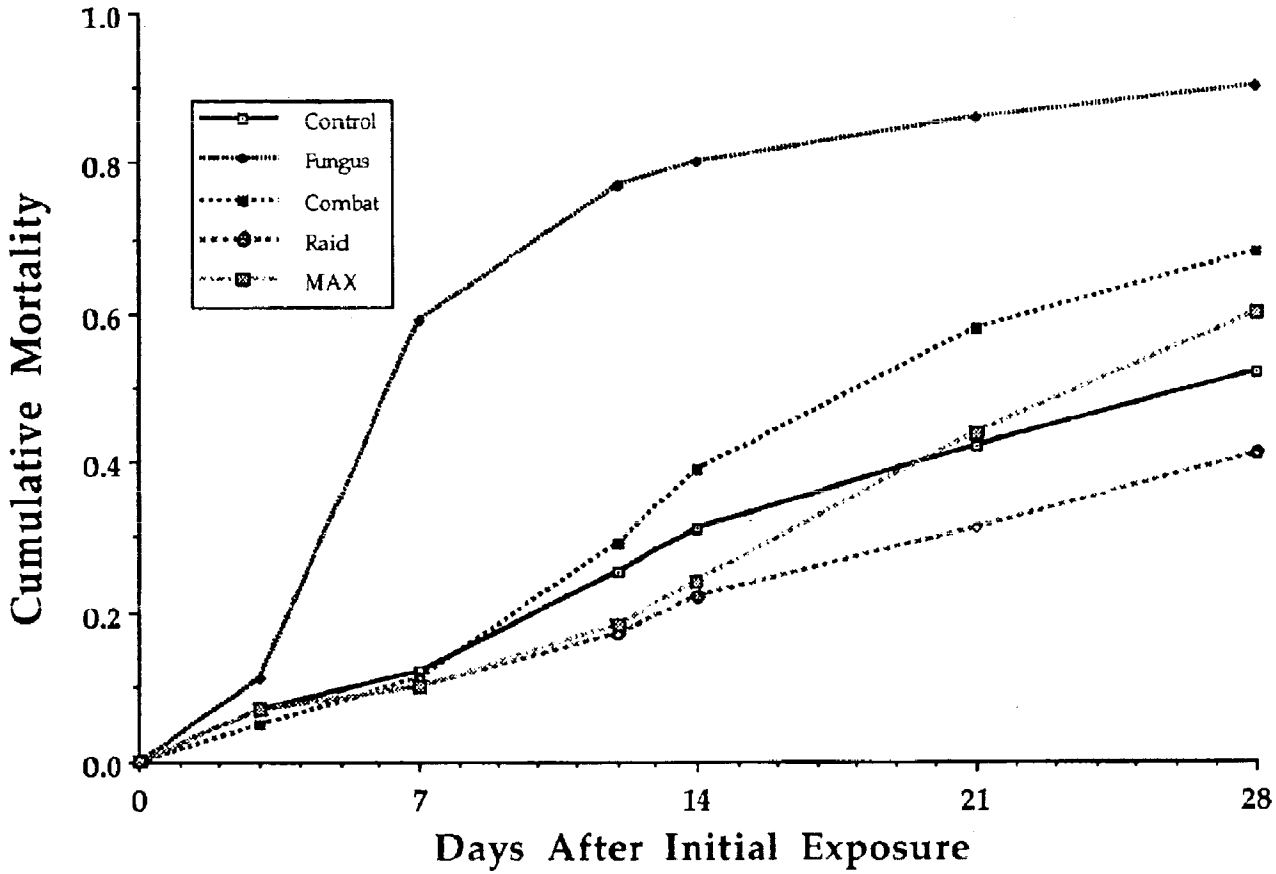
FIG. 9 shows a comparison of chemical baits from traps to fungus formulation for the control of crazy ants.

Chemical Baits from Traps Compared to Fungal Formulations for the Control of Crazy Ants The chemical baits which were compared are from: MAX ant trap, RAID ant trap, and COMBAT ant trap. The chemical baits were removed from traps and offered to ants on paper. The control received the same formulation as the fungus treatment but without conidia. The fungal formulation contained peanut material and cornstarch and 10% conidia of B. bassiana No. 447. In all experiments, the bait with Beauveria bassiana caused mortality similar or greater than that caused by chemical baits. See FIG. 9 for the results of one such experiment.

EXAMPLE 14

Figure 10:
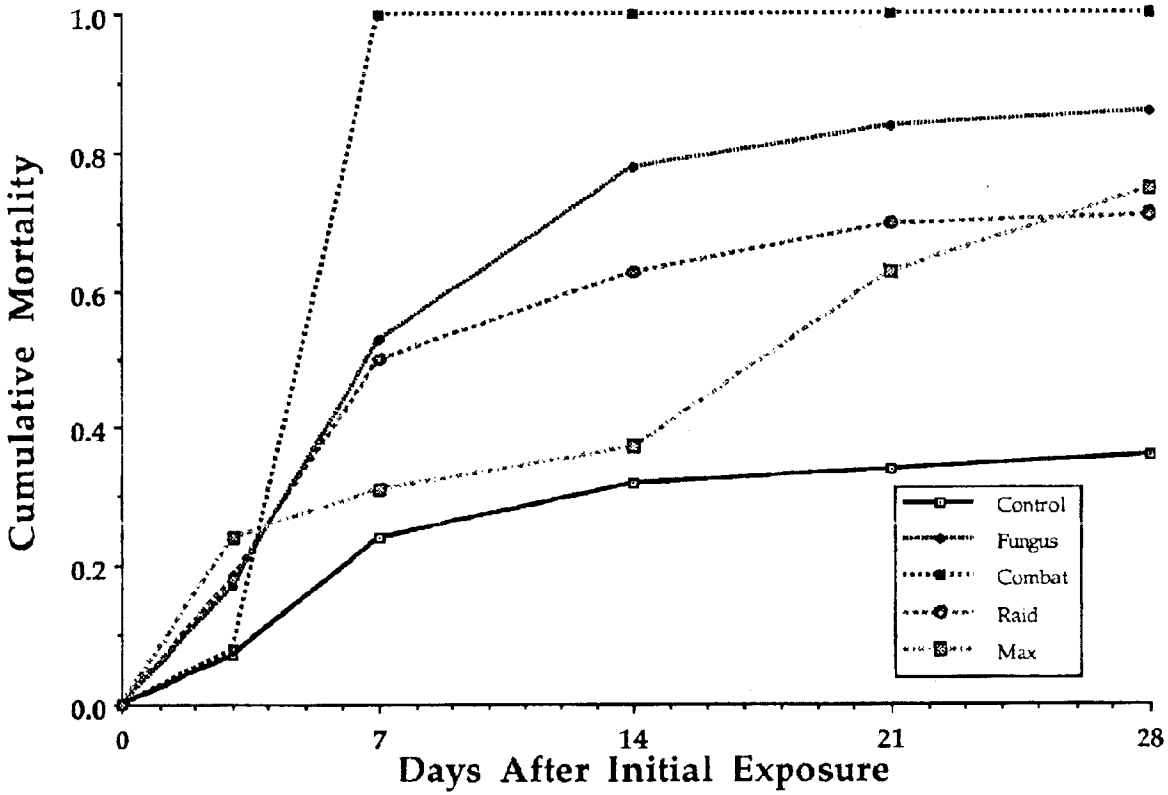
FIG. 10 shows a comparison of chemical baits from traps to fungus formulation for the control of carpenter ants.

Chemical Baits from Traps Compared to Fungal Formulation for Control of Carpenter Ants The chemical baits which were compared are from: MAX ant trap, RAID ant trap, and COMBAT ant trap. The chemical baits were removed from traps and offered to ants on paper. The control received the same formulation as the fungus treatment but without conidia. The fungal formulation contained peanut material and cornstarch and 10% conidia of B. bassiana No. 447. As can be seen from FIG. 10, the fungal formulation has performance similar to, or slightly better than, MAX and RAID baits, and only slightly less than COMBAT. Both COMBAT and the fungus had their effects delayed in relation to RAID and MAX, but the delay in fungal effect is longer than that of COMBAT.

EXAMPLE 15

Field Pesticides Compared to Fungal Formulations for the Control of Fire Ants AMDRO chemical baits were evaluated. The bait in one experiment also had 10% of an ACEPHATE fire ant powder insecticide. In each treatment, one-half gram of formulation was provided per arena on weighing paper. The formulation was removed after 4 days. The control received the same formulation as the fungus treatment but without conidia. The fungal formulation contained peanut material, cornstarch, and 10% conidia of B. bassiana No. 447.

Figure 11:
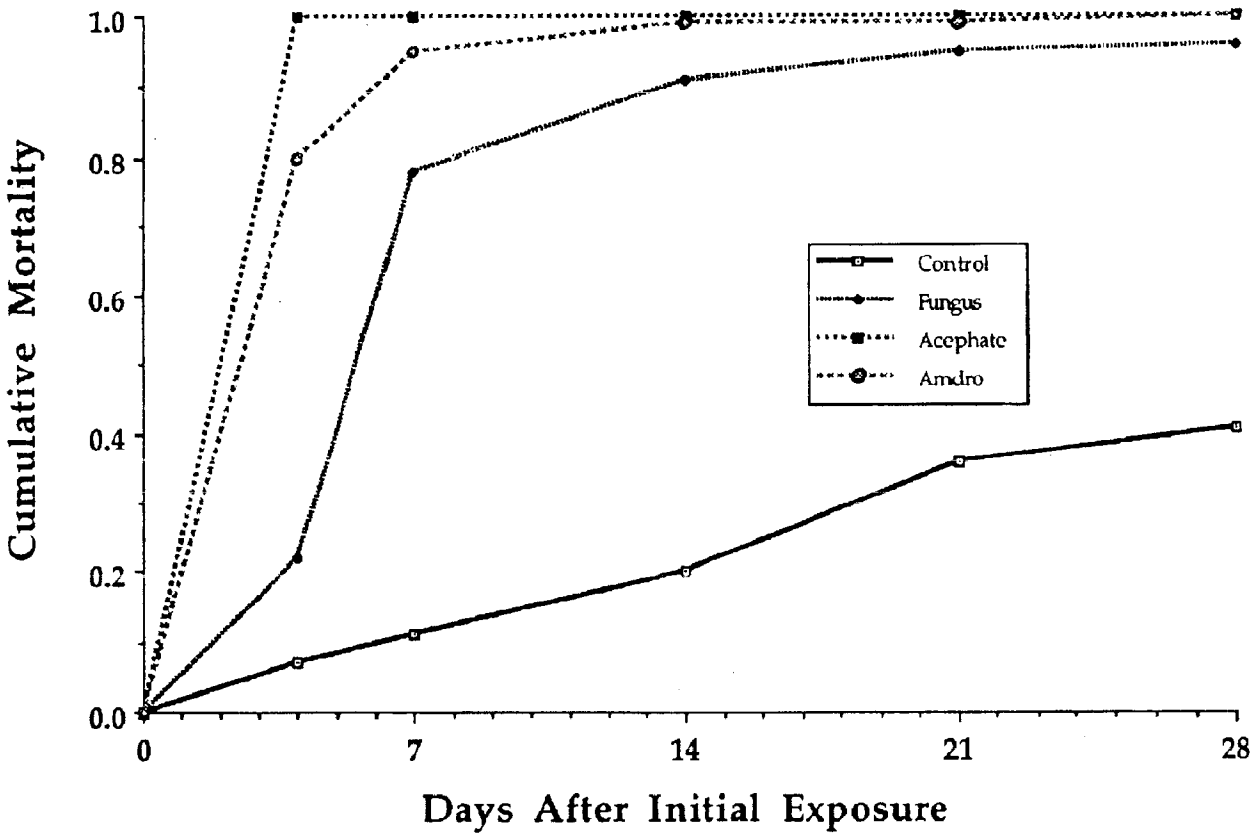
FIG. 11 shows a comparison of field pesticides to fungus formulation for the control of fire ants.

ACEPHATE (which is not normally a bait formulation) kills the ants almost immediately. Mortality with AMDRO increases less rapidly, but by day 4, ≈80% of the population was dead. Mortality with fungus increases at a slower rate but final mortality after 2–4 weeks is similar to that obtained with the chemical pesticides (FIG. 11).

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A composition for the control of a cockroach or ant pest comprising food source particles, a drying agent, and a biocontrol agent derived from an entomopathogenic fungi selected from the group consisting of spores and conidia and wherein said drying agent is a chemically acting drying agent, a physically acting drying agent, or combinations of more than one chemically acting and/or physically acting drying agent.

2. The composition, according to claim 1, wherein said entomopathogenic fungi is selected from the group consisting of Beauveria bassiana No. 447, having all of the identifying characteristics of ATCC 20872, and Beauveria bassiana SP111, having all of the identifying characteristics of ATCC 74038.

3. The composition, according to claim 2, wherein said Beauveria bassiana is isolate No. 447, having all of the identifying characteristics of ATCC 20872.

4. The composition, according to claim 2, wherein said Beauveria bassiana is isolate SP111, having all of the identifying characteristics of ATCC 74038.

5. The composition, according to claim 1, wherein said drying agent is a chemically acting drying agent.

6. The composition according to claim 5, wherein said chemically acting drying agent is selected from the group consisting of calcium chloride, sodium sulfate, or magnesium perchlorate, phosphorus pentoxide, sicacide, metals, and metal hydrides.

7. The composition, according to claim 1, wherein said drying agent is a physically acting drying agent.

8. The composition according to claim 7, wherein said physically acting drying agent is selected from the group consisting of $SiO_2$, synthetic zeolite, naturally occurring zeolite, aluminum oxide (alumina), drierite, calcium sulfate, calcium chloride, calcium oxide, sodium sulfate, copper (II) sulfate, potassium carbonate, and magnesium oxide.

9. The composition of claim 1, further comprising a pheromone or extract.

10. The composition of claim 7, further comprising a pheromone or extract.

11. The composition of claim 5, further comprising a pheromone or extract.

12. The composition of claim 5, wherein said composition can pass through a 60 mesh, or smaller, sieve.

13. The composition of claim 7, wherein said composition can pass through a 60 mesh, or smaller, sieve.

14. The composition of claim 1, wherein said composition can pass through a 60 mesh, or smaller, sieve.

15. A method of controlling a cockroach or ant pest comprising applying to the environment of the cockroach or ant pest, or directly onto the cockroach or ant pest, a composition comprising food source particles, a drying agent, and a biocontrol agent derived from an entomopathogenic fungi selected from the group consisting of spores and conidia and wherein said drying agent is a chemically acting drying agent, a physically acting drying agent, or combinations of more than one chemically acting and/or physically acting drying agent.

16. The method of claim 15, wherein said physically acting drying agent is selected from the group consisting of $SiO_2$, synthetic zeolite, naturally occurring zeolite, aluminum oxide (alumina), drierite, calcium sulfate, calcium chloride, calcium oxide, sodium sulfate, copper (II) sulfate, potassium carbonate, and magnesium oxide and said chemically acting drying agent is selected from the group consisting of calcium chloride, sodium sulfate, or magnesium perchlorate, phosphorus pentoxide, sicacide, metals, and metal hydrides.

17. The method according to claim 15, wherein said entomopathogenic fungi is selected from the group consisting of Beauveria bassiana No. 447, having all of the identifying characteristics of ATCC 20872, and Beauveria bassiana SP111, having all of the identifying characteristics of ATCC 74038.

18. The method according to claim 15, wherein said composition further comprises a pheromone or extract.

19. The method according to claim 15, wherein said composition can pass through a 60 mesh, or smaller, sieve.

20. The method according to claim 16, wherein said composition can pass through a 60 mesh, or smaller, sieve, and, optionally, further comprises a pheromone or extract.

* * * * *